United States Patent [19]

Schmidt et al.

[11] Patent Number: 5,613,663
[45] Date of Patent: Mar. 25, 1997

[54] VALVE DEVICE

[75] Inventors: Klaus J. Schmidt, Ahnatal; Juergen Fuchs, Bad Emstal; Heinz Wiegel, Alheim, all of Germany

[73] Assignee: B. Braun Melsungen AG, Melsungen, Germany

[21] Appl. No.: 534,444

[22] Filed: Sep. 27, 1995

[30] Foreign Application Priority Data

Nov. 29, 1994 [DE] Germany ............ 44 42 352.7

[51] Int. Cl.⁶ ........................... F16L 29/00
[52] U.S. Cl. ............ 251/149.2; 604/167; 604/256
[58] Field of Search ............ 251/149.2, 149.1, 251/298, 301; 604/167, 256, 264, 905, 280, 283

[56] References Cited

U.S. PATENT DOCUMENTS 4,842,591  6/1989  Luther ......................... 604/905 X
5,044,401  9/1991  Giesler et al. ............... 251/149.2 X
5,125,903  6/1992  McLaughlin et al. .......... 251/149.1 X
5,456,675  10/1995  Wolbring et al. ............. 604/256 X

FOREIGN PATENT DOCUMENTS 261317  3/1988  European Pat. Off..
2817102  10/1979  Germany.

*Primary Examiner*—Kevin Lee
*Attorney, Agent, or Firm*—Loeb & Loeb LLP

[57] ABSTRACT

In a valve device in a connection piece, it is provided that the valve body is configured as a valve flap (20) with a closed surface, which valve flap is mounted in the connection piece via an elastic radial tongue (21) and rests against an annular supporting surface (26) in the closed position, and that the sliding member pivots the valve flap (20) in opening direction about the radial tongue (21) by pressure against its closed surface.

10 Claims, 4 Drawing Sheets

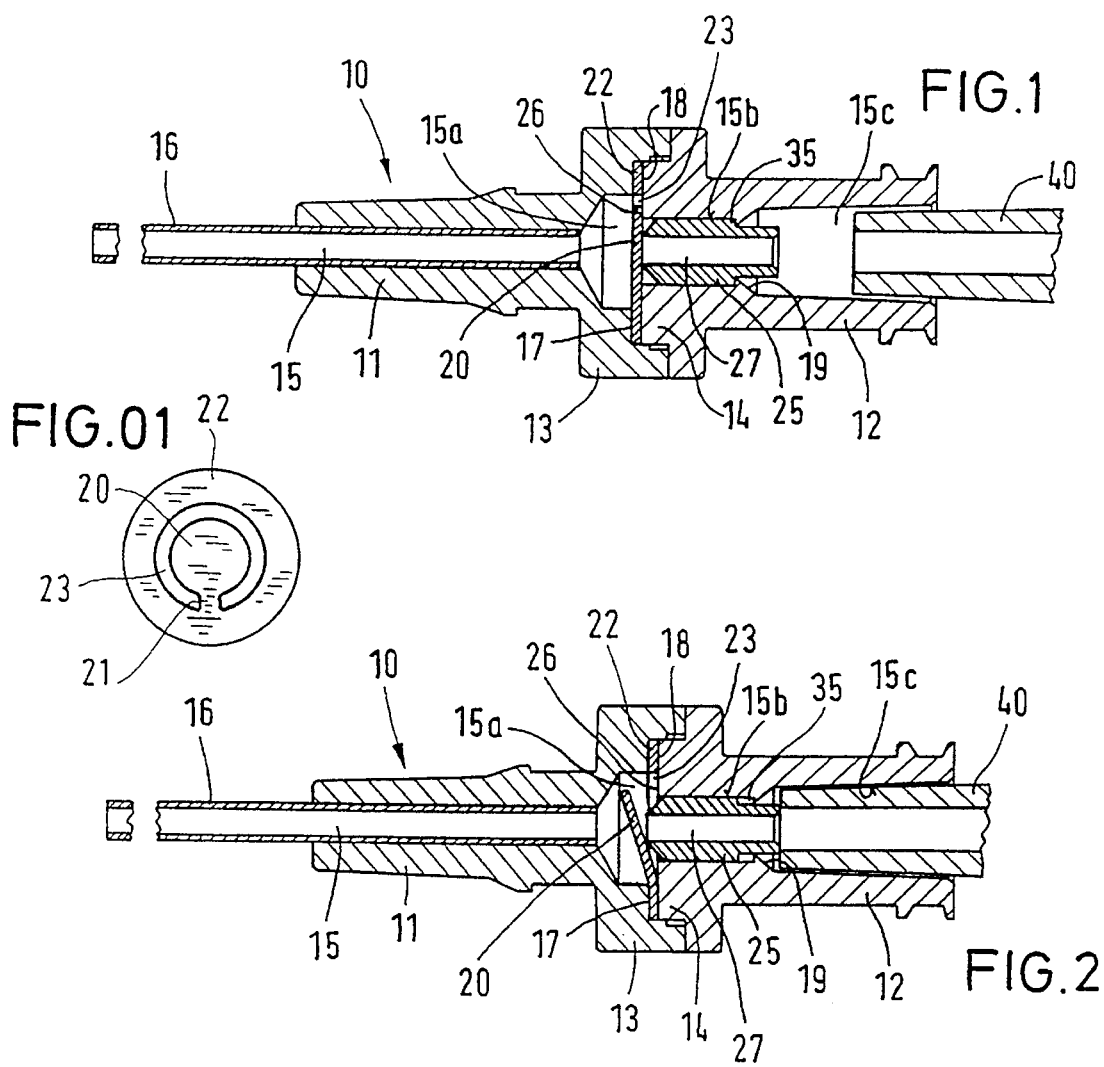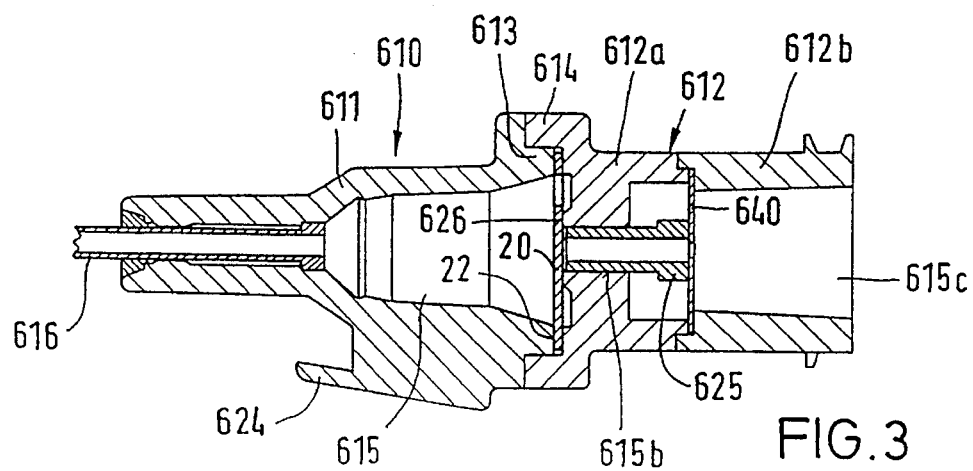

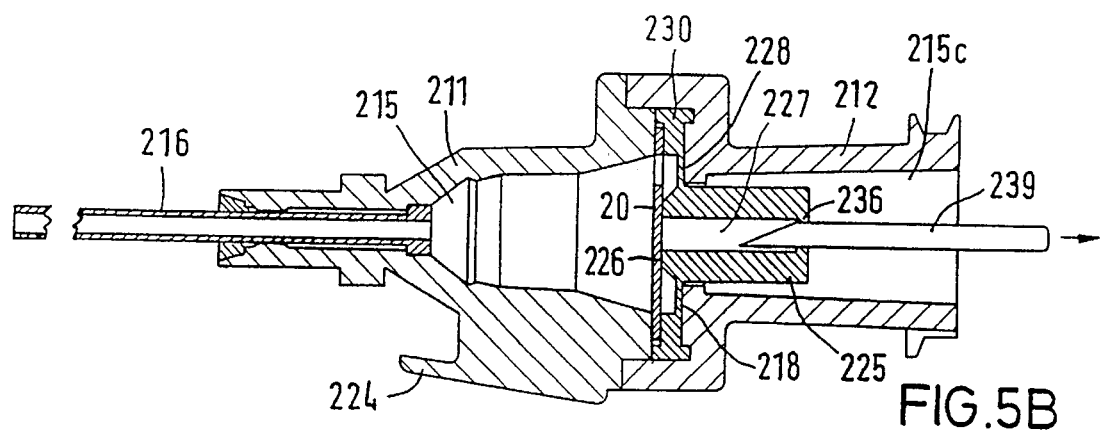
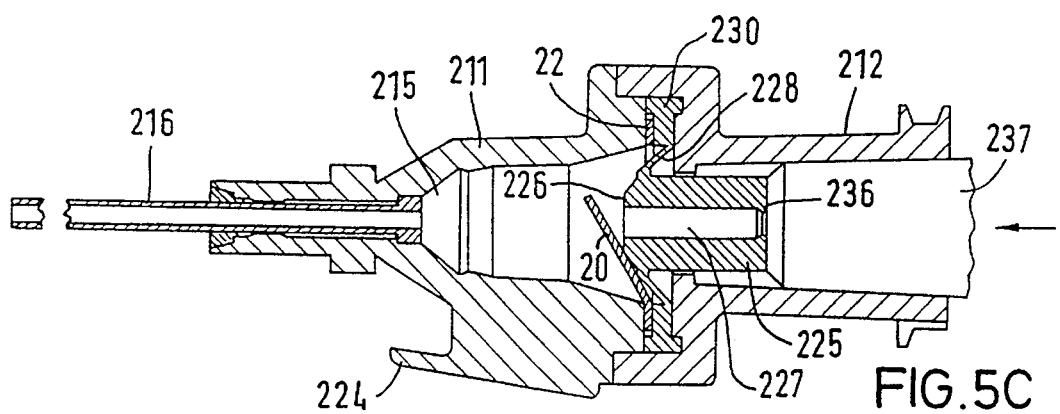
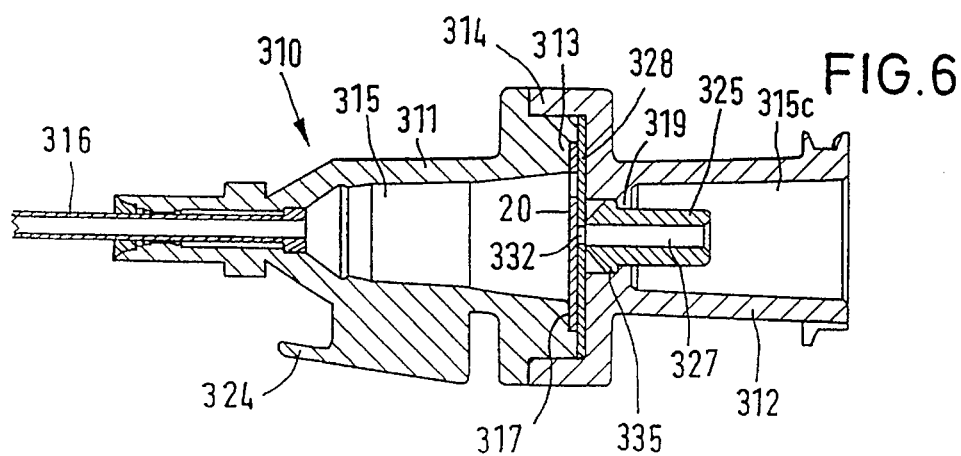

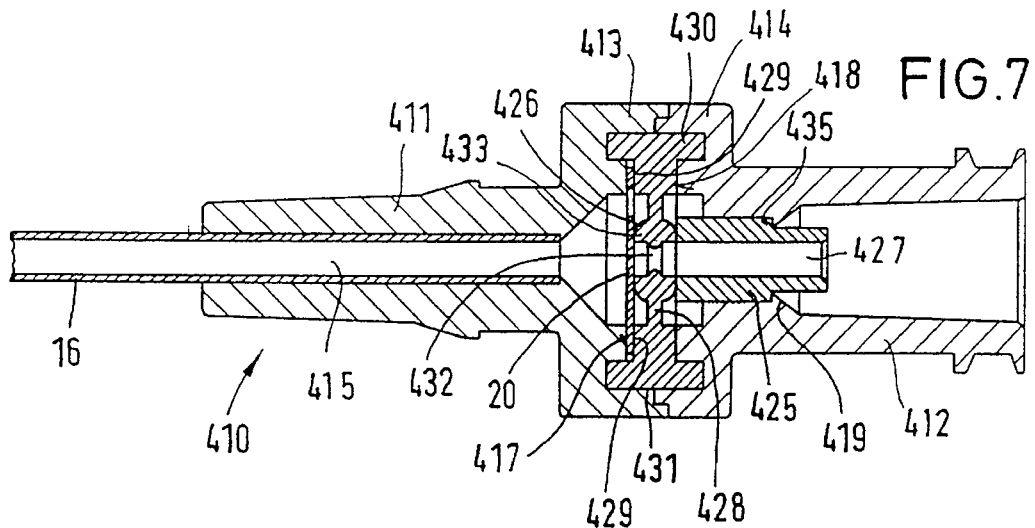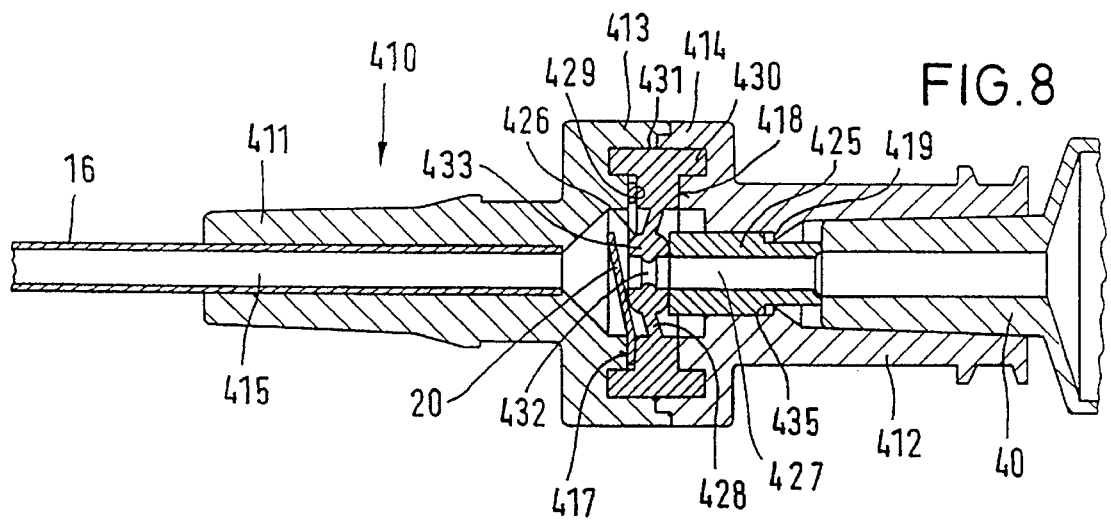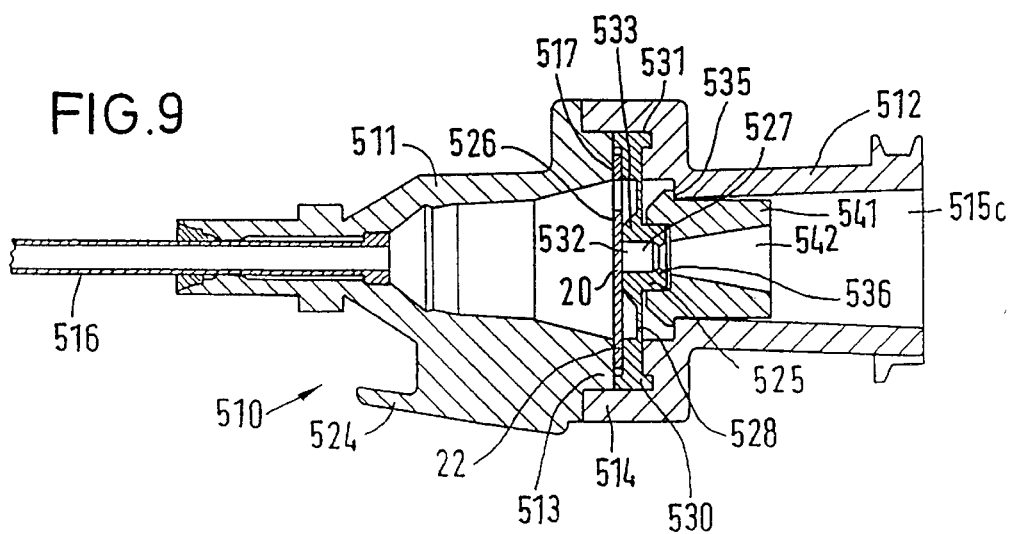

VALVE DEVICE

BACKGROUND OF THE INVENTION

The invention relates to a valve device in a connection piece comprising a flow channel which is open at its front and rear ends and wherein a valve body is arranged which can be brought into its opened position by means of an axially displaceable sliding member.

Generally, connection pieces with valve device are installed in a conduit whose channel is to be transmissive in one direction and closed in the opposite direction. The term "conduit" is meant to comprise rigid and flexible cannulas as well as flexible catheters placed in the body of a patient on one end and hose lines of infusion and transfusion devices, pressure measuring conduits as well as syringes at the other end of the connection piece, the valve device being intended for permitting an unhindered supply or collection of liquid and for effecting an automatic closure when the desired liquid flow stops, so that neither body secretion contaminates the surroundings of the connection piece nor air enters into the body of the patient. Both is dangerous for the patient because it gives rise to bacterial infections and the danger of embolism, and the former may also harm the operator by the transfer of germs.

In an arterial puncture, e.g., such valve devices have the task of holding back the blood located in the catheter with an over-pressure 100–200 mm Hg with respect to atmosphere when the sharpened steel cannula is withdrawn from the catheter after a successful puncture of the artery. Furthermore, the valve must open and permit the flow of blood or a flowing medium as soon as the Luer cone of a connection conduit is connected to the connection piece in order to collect blood samples or to measure the blood pressure via a liquid column.

From German Patent DE 28 17 102 C2, a connection piece with a valve device is known, wherein the valve body consists of a disc of elastomer material with a central slot. In the flow channel, a body being displaceable relative to the disc is supported, which is advanced by the connection cone of an infusion tube and at least partially penetrates the slot when in advanced position in order to spread and keep it open. Upon release of the sliding portion from the connection cone, the elastically deformable disc is to press back the sliding portion, the slot being intended to sealingly close. The closing speed and impermeability of the valve device depend on the readjusting capability of the disc material and the soundness of the slot flaps. Therefore, the effectiveness is reduced by material fatigue. The latter results from repeated opening of the valve device during a long-term use of the connection piece. In addition, it becomes noticeable when using the arrangement, e.g., in an aspirating set with an enclosed steel cannula. In this case, the steel cannula deforms the closed slot lips over a longer period of time, and by the plastic deformation, a hole is created which does not close after withdrawal of the steel cannula, so that body secretion escapes to the outside through the hole in the slot closed per se. Besides, the known valve device is not reliable at higher internal pressures, e.g., arterial pressure (pressure of 200 mm water column), because there is the danger that the internal pressure curves the slotted center of the disc outwards, so that the slot lips do not firmly abut each other on their entire thickness but diverge outwards. Thereby, the sealing surface is reduced such that the arterial pressure can press blood to the outside and a medium for bacterial growth is created, which is carried on into the patient and imports bacterial infections.

A valve device known from European Patent Application EP-A-0 261 317 also operates with a push-open mechanism, and its closing efficiency depends on the restoring capability of the valve body configured as a closed elastomer disk. With its inner surface, the elastomer surface lies upon a bearing tip arranged in the flow channel, and a sliding member comprising two fork legs pressing against the edge zone of the elastomer disk to press it away from an annular valve seat in order to open the flow channel acts against its outer surface. Although this known valve device is tight in backflow direction even at high internal pressures, it does not unblock a central channel through which an elongate object such as a steel cannula, a guide wire or a catheter could be guided, and therefore, it is unsuitable for this broad medical product range.

SUMMARY OF THE INVENTION

It is an object of the present invention to configure a valve device in a connection piece in such a manner that the connection piece is universally applicable and stands out due to reliable impermeability at higher pressures in reverse flow direction as well as after extended storage times with an elongate member enclosed therein.

This object is solved, according to the invention, by configuring the valve body as a valve flap having a closed surface and being mounted in the connection piece via an elastic radial tongue and resting against an annular supporting surface in the closed position, and by the sliding portion pivoting the valve flap in opening direction about the radial tongue by pressing against the closed surface thereof.

This valve device operates as flap valve with a push-open mechanism, so that opening is not only possible for the supply of liquid, but also for collection. The restoring of the valve flap in closing position is achieved by the internal body pressure which presses the valve flap firmly against the annular supporting surface. The lack of perforation of the valve flap offers no possibility for the formation of leakage openings at higher internal pressures. The channel closure functions reliably and becomes the tighter the higher the internal pressure is. Suspending the valve flap on the radial elastic tongue frees it of any inertia forces and it closes virtually without any delay in that moment where the internal pressure arises, i.e., where backflowing liquid meets the valve flap. The closure action of the valve flap is independent of its proper elasticity and the restoring capability of its material, so that it can be opened as often as desired without a change in closing efficiency arising. The outside of the connection piece remains clean and patient and operator are not infected by body fluid. Since the valve flap is mounted in the connection piece only via the narrow elastic radial tongue, it loosely hangs next to an elongate member (steel cannula or mandrin) when the device is used in a vascular catheter, and it is not deformed thereby at all. Therefore, it functions fully and reliably even if the valve device is installed in a connection piece for a catheter set with an inserted steel cannula or enclosed guide wire, the diameter of the elongate member being irrelevant and the valve device thus being suitable for steel cannulas with a large outer diameter as well.

The sliding member may be an outer cone of a coupling element or syringe. In this case, the connection piece is dimensioned to be very small and the production costs are low since additional installations are omitted.

In an advantageous embodiment of the invention, the sliding member is designed as a tubular body being displaceably arranged within the flow channel and being secured against dropping out therein. The tubular body is advanced by means of a syringe cone or an outer cone of a conduit coupling assembly to lift off the valve flap from the annular supporting surface and unblock the flow channel from the outside to the inside. Since the valve flap suspended on the elastic radial tongue offers virtually no resistance against the pressure of the tubular body, the latter does not need to have any particular stability characteristics and it can be a light thin-walled portion. The expenditure of force upon displacing the sliding portion is extremely low.

The embodiments according to claims 10 and 11 form sealings effective when using an inserted elongate member in order to bridge the time during the withdrawal of the elongate member up to the complete closure of the valve flap. The sealing lip and the sealing disc, respectively, form a sealing around the steel cannula or the mandrin so that the escape of blood is prevented when withdrawing the elongate member as long as its tip is still located in the region of the valve flap.

The annular supporting surface may form part of the connection piece. It is also possible to configure the supporting surface on a centrally perforated sealing membrane being arranged between the valve flap and the sliding portion and being mounted in the connection piece at its edge. By a flat large contact surface for the valve flap, the sealing membrane provides for an increase in the sealing effect at the valve flap, on the one hand, and, on the other hand, it keeps the valve flap free of direct contact with the sliding member, so that its sealing surface is free of scratches and pressure traces. Besides, it accelerates the return of the valve flap to the closed position by elastically pressing the tubular body back by its membrane elasticity, so that the valve flap, onto which the internal body pressure acts, comes into immediate abutment on a supporting surface located in its closing plane and is tight without any canting.

The sealing membrane may be a disc of elastomer material. It is preferred that the disc is flat on both sides. Alternatively, it may comprise a thick-walled outer flange edge received in an inner circumferential groove of the connection piece. At least on that side of the sealing membrane facing the valve flap, a torus surrounding the central perforation is configured which serves as supporting surface for the valve flap.

The tubular body can be formed integrally with the sealing membrane. This is favorable under the aspects of production and installation, because the tubular body is centered and precisely fittingly accommodated in the connection piece simultaneously with the mounting of the sealing membrane. Besides, sealing problems at the guidance of the tubular body are eliminated.

The valve flap and the elastic radial tongue can be made of different materials. The valve flap may consist of rigid material and cooperate with an elastic annular supporting surface. It is important that the radial tongue is elastic, so that it offers no resistance to the movement of the valve flap under the influence of the sliding member or the backflowing fluid. In an advantageous embodiment of the invention, it is provided that the radial tongue connects the valve flap with an outer ring, that the tongue, the valve flap, and the outer ring are integrally formed of elastic flat material, and that the outer ring is clamped between ring surfaces in the connection piece so that it outwardly seals two assembled housing parts when arranged therebetween.

Further useful embodiments of the invention are characterized in the subclaims.

BRIEF DESCRIPTION OF THE DRAWINGS

Hereinafter, embodiments of the invention are explained with reference to the drawing, in which FIG. 01 shows a plan view of the valve flap arrangement used for all embodiments, FIG. 1 is a longitudinal section of a connection piece with a first embodiment of a valve device in the closed state, FIG. 2 shows the valve device in the opened state, FIG. 3 is a longitudinal section of a connection piece of a second embodiment of a valve device in the closed state, FIGS. 5, 5A, 5B, 5C are longitudinal sections of a connection piece with a fourth embodiment of a valve device in four different states, FIG. 6 is a longitudinal section of a connection piece with a fifth embodiment of a valve device in the closed state, FIG. 7 is a longitudinal section of a connection piece with a sixth embodiment of a valve device in the closed state, FIG. 8 shows the valve device according to FIG. 7 in the opened state, and FIG. 9 is a longitudinal section of a connection piece with a seventh embodiment of a valve device.

DESCRIPTION OF THE PREFERRED EMBODIMENTS

Figure 4:
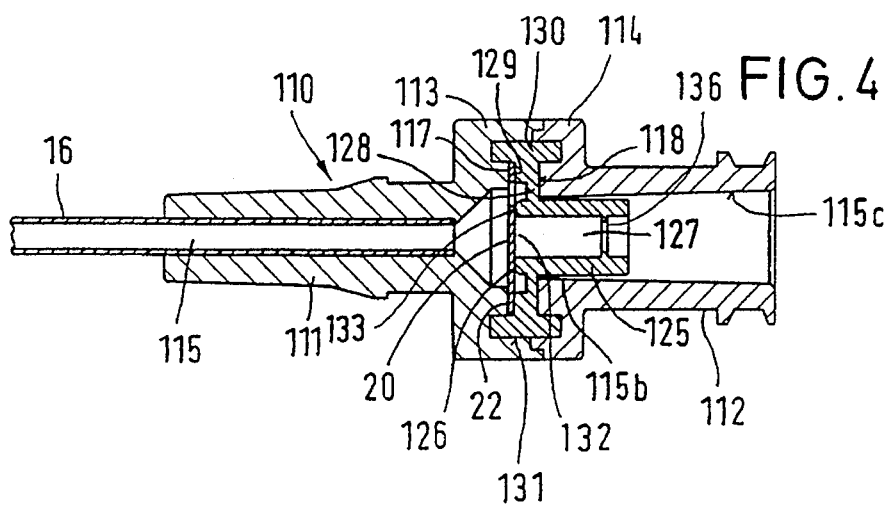
FIG. 4 is a longitudinal section of a connection piece with a third embodiment of a valve device in the closed state.

The embodiment of FIGS. 1 through 3 shows the simplest version of a valve device with installed sliding member in a connection piece. The connection piece 10 consists of an upper housing part 11 and a lower housing part 12 of plastic, which are interconnected at flange-like plug portions by ultrasonic welding. Coaxial passages forming a flow channel 15 of the connection piece 10 open at both ends extend through the upper housing part 11 and the lower housing part 12. At the outer end of the lower housing part 12, there are projections of a Luer lock locking mechanism. In a circular cylindrical section of the flow channel 15 in the upper housing part 11, a rigid or flexible cannula is mounted which may either be a steel cannula with a sharp tip or a catheter tube 16. In its middle section 15a, the flow channel 15 is enlarged. From there, it rearwardly continues as a narrower circular cylindrical guide section 15b adjacent to which a rearwardly open inner cone 15c is arranged.

In the connection piece 10, a valve device is accommodated. In all embodiments, it consists of a circular valve flap 20, as shown in FIG. 3, which is connected to an outer ring 22 via a radial tongue 21, an annular space 23 ending at the two straight flanks of the radial tongue 21 being located between the outer periphery of the valve flap 20 and the inner periphery of the outer ring 22. The entire arrangement 20 through 23 is integrally formed of elastic flat material. With respect to the outer ring 22, the valve flap 20 is movable transversely to the plane of said ring, the small width of the radial tongue 21 virtually offering no resistance against the movement and substantially serving as holding and centering element. The outer ring 22 is clamped between two ring surfaces 17 and 18 of the upper housing part 11 and the lower housing part 12, so that it cannot be displaced. The radial width of the ring surface 17 matches the outer ring 22. In the guide section 15b of the flow channel 15, a tubular body 25 is provided so as to be axially displaceable and concentric with the valve flap 20 and comprises a step 35 at its rear end, which engages with a stop rib 19 at the rear end of the guide section 15b so that the tubular body 25 does not fall out of the flow channel 15. In this position, the tapered front end of the tubular body 25 abuts the back side of the valve flap 20 which closely rests against an annular supporting surface 26 on the plug portion 14 of the lower housing part 12. This has the advantage that the tubular body need not be sealed in the guide section 15b in addition to the lower housing part 12 and a very slight slide fit can be performed. The tubular body 25 is made of plastic and extending therethrough is a bore 27 whose diameter approximately corresponds to the diameter of the lumen of the catheter tube 16. The rear end of the tubular body 25 is blunt and projects into the inner cone 15c over a short length.

After a blood vessel, into which the catheter tube 16 is to be introduced, has been punctured by means of a steel cannula pushing aside the valve flap 20 and projecting through the flow channel 15, the steel cannula is removed and backflowing blood meets with the valve flap 20. The blood reflux presses the valve flap 20 against the supporting surface 26 on the plug portion 14 and closes the flow channel 15. In order to open the valve flap 20 for fluid supply from outside or fluid collection from inside, a matching hollow outer cone 40, which may form part of a syringe or a coupling assembly establishing a connection between the catheter tube 16 and a hose line leading to a liquid transfer apparatus or a measuring instrument (FIG. 2), is inserted into the inner cone 15c. The outer cone 40 is advanced into the inner cone 15c until it meets with the rear end of the tubular body 25 and advances the latter a bit forward. In doing so, the valve flap 20 is pivoted about the radial tongue 21 and lifted off from the supporting surface 26. Under the pressure of the liquid flowing from the back, the valve flap 20 suspended on the radial tongue 21 is further pressed aside in the enlarged middle section 15a and the entire cross section of the flow channel 15 is available to the liquid flow. As soon as the liquid flow in the patient's body has ceased and the outer cone 40 is decoupled from the connection piece 10, backflowing blood enters into the catheter tube 16, presses against the valve flap 20 and presses it against the supporting surface 26 on the lower housing part 12, the tubular body 25 assuming its rearward stop position. The higher the internal pressure, the tighter is the closure. Virtually no blood enters into the inner cone 15c through the bore 27.

The valve device according to the second embodiment according to FIG. 3 is installed in a connection piece 610 with a flow channel 615 comprising tangentially adjacent lateral wings 624 for fastening on the skin and being suitable as hub of an artery cannula 616. The connection piece 610 consists of an upper housing part 611 and a lower housing part 612, the lower housing part 612 being assembled from a front piece 612a and an end piece 612b which hold, in a tightly clamped manner, a centrally perforated sealing disc 640 between plug portions, said sealing disc being provided for the passage of a steel cannula or a mandrin. Plug portions 613 and 613, which may be interconnected by ultrasonic welding, serve to connect the upper housing member 611 with the lower housing member 612. The outer ring 22 of the valve flap 20 is firmly clamped between ring surfaces 617 and 618 of the upper housing member 611 and the lower housing member 612.

Extending coaxially with the closed valve flap 20 in the flow channel 615, there is a tubular body 625 being displaceable within a cylindrical guide section 615b and—as explained in connection with FIGS. 1 and 2—serves to open with the valve flap 20 and to release it for closing in the case of blood reflux. In the closed state, the valve flap 20 rests against a supporting surface 626 configured on an inner front face of the front piece 612a. The rear end of the tubular body 625 is supported on the sealing disc 640 which rearwardly seals the flow channel 615 when the elongate member is pushed through. An outer cone similar to the outer cone 40 according to FIGS. 1 and 2, which is plugged into the conical opening 615c of the end piece 612b behind the sealing disc 640, presses against the elastic sealing disc 640 and therethrough against the tubular body 625, whereby the valve flap 20 is opened in accordance with the constellation illustrated in FIG. 2. In this state, it is lifted off from the annular supporting surface 626. Blood reflux closes the valve flap 20 again and returns the tubular body 625.

The valve device of the embodiment shown in FIG. 4 is similar to that of the embodiment of FIG. 1. Here as well, a connection piece 110 having a catheter tube 16 and a flow channel 115 has the valve flap 20 installed therein, which is connected to the outer ring 22 via the radial tongue 21 (FIG. 01). In this embodiment, a tubular body 125 with a coaxial bore 127 is made of elastic material and integrally formed with a sealing membrane 128 provided with a hole 132 concentric with the bore 127 and surrounded by a torus 133 comprising the supporting surface 126. At the rear end of the tubular body 125, an inwardly directed radial sealing lip 136 is configured which serves as a circumferential sealing for a mandrin or a steel cannula which can be pushed through the flow channel 115. The sealing membrane 128 comprises a thick-walled outer flange edge 130 extending to both sides in axial direction and being received in a matching inner circumferential groove 131 in plug portions 113,114 in the separation zone between the upper housing part 111 and the lower housing part 112 of the connection piece 110.

The unit of the tubular body 135 and the sealing membrane 128 is installed together with the valve flap arrangement 20–23 before the two housing parts 111 and 112 are connected and welded together. This mounting is very simple and guarantees a precise fit of the parts. The outer ring 22 of the valve flap arrangement is clamped between the ring surface 117 of the upper housing part 111 and a front face 129 of an axially projecting radial section of the sealing membrane 128, said front face being located radially inwards adjacent the flange edge 130. The back side of the sealing membrane 128 is flat and rests against a circular ring surface 118 of the lower housing part 112. The sealing membrane 128 seals the transition at the clamping site of the valve flap arrangement and keeps the guidance 115b for the tubular body 125 free of body secretion. Besides, the sealing membrane 128 has the task to speedily displace the tubular body 125 backwards by its membrane elasticity when it is released from the outer cone 40. Thus, the return speed of the valve flap 20 is increased under the pressure of the backflowing blood.

The embodiment of FIGS. 5, 5A, 5B, 5C shows the valve device with a connection piece 210 with tangentially adjacent lateral wings 224 for fastening on the skin, said connection piece being suitable as a hub for fastening a plastic cannula or a catheter 216. The connection piece 210 is composed of an upper housing part 211 and a lower housing part 212, which are plugged together on plug portions 213,214 and interconnected, preferably by ultrasonic welding. Extending through the connection piece 210 is a through channel 215 which is rearwardly enlarged by section in the region of the upper housing part 211 and is designed, in the region of the lower housing part 212, as an inner cone 215c for connecting an outer cone 237 of a syringe or a coupling assembly of a hose line or a hub 238 of a steel cannula 239. At the rear end of the inner cone 215c, outwardly directed thread portions of a Luer lock locking are located.

In the connection zone between the upper and the lower housing part 211 and 212, the valve flap 20 with the outer ring 22 (FIG. 01) is arranged. The outer ring 22 is clamped between a ring surface 217 of the upper housing part 211 and a front face 229 of a flange edge 230 which forms part of a sealing membrane 228. The sealing membrane 228 is integrally formed with a circular cylindrical tubular body 225 of elastomer material, so that a complete axial sealing is achieved by radially bridging the flow channel 215. Its outer thick flange edge 230 is received in a matching inner circumferential groove 231 of the upper housing part 212. Extending through the tubular body 225 is a bore 227 which is arranged coaxially with a hole 232 in the middle of the sealing membrane 228. On the side facing the valve flap 20, the hole 232 is surrounded by a torus 233 with the supporting surface 226. With the greatest part of its length, the tubular body 225 projects into an inner cone 215c of the lower housing part 212. An axially short cylindrical guide section 215b serves as guidance for the tubular body 225. The inner edge of the guide section 215b is adjacent a circular ring surface 218 directed radially outward. The latter serves as abutment surface for the sealing membrane 228. At the rear end of the tubular body 225, there is a sealing lip 236 directed radially inwards and narrowing the bore 227.

The outer ring 22 of the valve flap 20 is positively connected with the sealing membrane 228 arranged therebehind and thus forms the outer sealing of the two-part connection piece 210. In the region of the housing sealing, the tubular inner body 225 of the sealing membrane 228 forms the liquid-proof sealing toward the inner cone 215c by means of its front face in cooperation with the valve flap 20.

Figure 5:
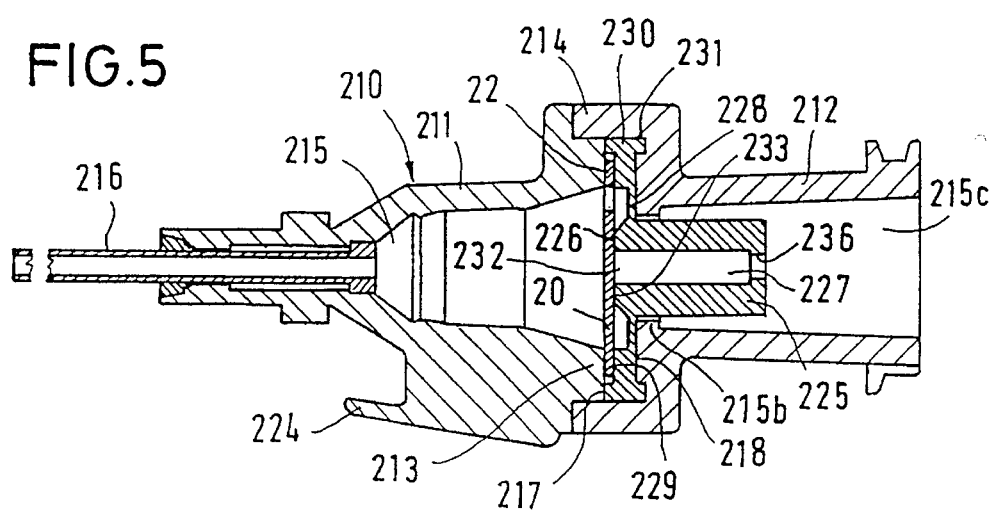
Figure 5A:
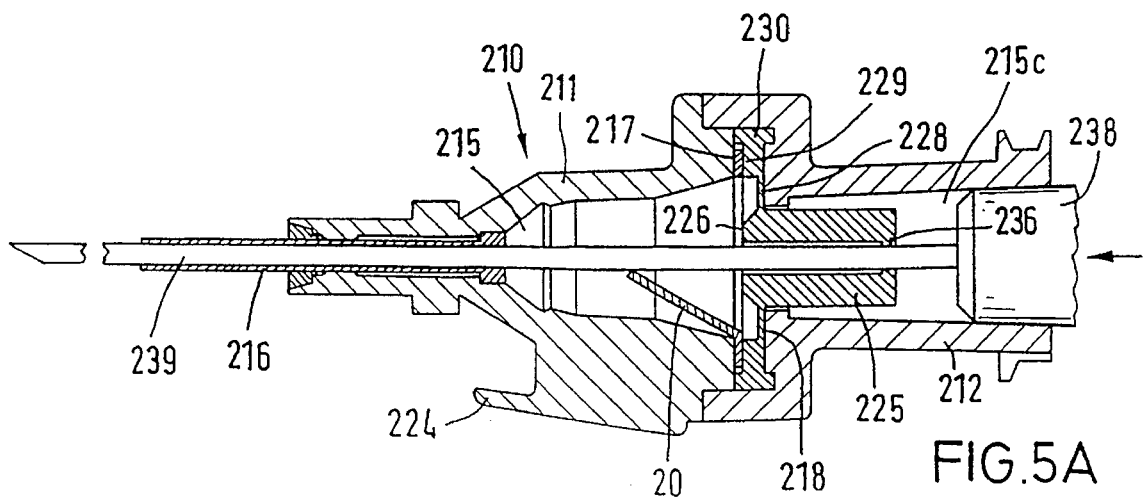

When puncturing a vessel, the annular sealing lip 236 seals the steel cannula 239 which extends through the connection piece 210 and the catheter 216 and pushes the valve flap 20 aside when in opened position (FIG. 5A). When withdrawing the steel cannula 239, the sealing lip 236 is effective until the complete ground bevel of the cannula has passed the valve flap 20 (FIG. 5B). Through the liquid pressure of the arterial blood, the valve flap 20 is directly pressed onto the sealing surface of the sealing membrane 238 upon withdrawal of the steel cannula 238 and thus prevents blood from escaping. When such a catheterization set is new, the valve flap 20 hangs loosely beside the steel cannula and remains free of any deformations which might cause sealing problems later on.

As soon as an outer cone 237, e.g., of a pressure line or selector valve, is plugged into the inner cone 215c, the front face of the outer cone 237 presses the tubular body 225 toward the catheter tip or vessel access and thus lifts the valve flap 20 off from the supporting surface 226, so that the liquid medium can flow through the flow channel 216 in forward direction or the blood can flow through the flow channel 215 in rearward direction (FIG. 5C).

After withdrawal of the outer cone 237 and in the original position in the new state, the tubular body 225 assumes the return position shown in FIG. 5, in which its front end forming the supporting surface 226 for the valve flap 20 is withdrawn into the plane of the back surface of the valve flap 20 and a tight closure of the flow channel 215 is achieved at internal pressure acting against the valve flap 20.

According to FIG. 6, a connection piece 310 is assembled from a upper housing part 311 and a lower housing part 312. A stop rib 319 directed radially inwards in the lower housing part 312 defines the retreated position of a tubular body 325 configured as a piece part and comprising a bore 327, said body resting, in its original position, against the stop rib 219 with an outwardly directed step 335. The stop rib 319 has an axially short circular cylindrical guide section for the circular cylindrical shank portion of the tubular body 325. In the original position, the front conical end of the tubular body 325 abuts a sealing membrane 328 configured as a flat disc and having a central hole 332 whose diameter substantially corresponds to the diameter of the bore 327 of the tubular body 325. The outer edge of the sealing membrane 328 is compressed between fitting surfaces of the plug portion 314 of the lower housing part 312 and of the plug portion 313 of the upper housing part 311. With its mounting 21,22, the valve flap 20 flatly rests against the sealing membrane 328. Its outer ring 22 is pressed against the edge zone of the sealing membrane 328 by the ring surface 317 of the plug portion 313, said edge zone being supported on the front face of the lower housing part 312.

When plugging an outer cone 40 into the inner cone 315c, the tubular body 325 is forwardly displaced, the center of the sealing membrane 328 is curved outward and presses the valve flap 20 into the flared portion of the flow channel 315 so that the hole 332 is unblocked and a free flow through the artery cannula 316 is permitted. After withdrawal of the outer cone 40, the elasticity of the sealing membrane 328 pushes the tubular body 325 back immediately so that the valve flap 20, upon which the backflowing blood acts, meets with the absolutely flat supporting surface on the sealing membrane 328 and immediately closes the hole 332. The surface contact between the valve flap 20 and the sealing membrane 328 provides for excellent sealing.

The embodiment of FIGS. 7 and 8 employs a connection piece 410 similar to the connection piece 110 of FIG. 4, whose upper housing part 411 comprises a catheter tube 16 in a flow channel 415. In the connection zone between the upper housing part 411 and the lower housing part 412, a circumferential groove 431 for receiving a thick-walled outer flange edge 430 of a sealing membrane 428 is configured in plug portions 413 and 414. The sealing membrane 428 consists of elastomer material. Adjacent the flange edge 430, there is an annular body directed radially inwards whose outer surface rests against a ring surface 418 of the lower housing part 412 and whose inner surface forms a front face 429 against which the outer ring 22 of the valve flap arrangement (FIG. 3) is pressed by the ring surface 417 of the upper housing member 411. A thin section of the sealing membrane 428 adjacent the annular body is centrally provided with a hole 432 which is concentric with the bore 427 of the tubular body 425 and surrounded by a spherical torus 433 on both sides thereof. On the outside, the torus 433 forms an elastic abutment for the front face of the tubular body 425 which is a separate plastic member comprising a step 435 at its rear end, said step engaging with a stop rib 419 of the lower housing member 412 when the sealing membrane 428 and the valve flap 20 have assumed the original position (closed position) shown in FIG. 7. The forwardly directed inner portion of the torus 433 serves as supporting surface 426 for the valve flap 20 and provides for elastic sealing when the backflow of the blood sets in. The spherical configuration of the torus 433 in the region of the radial tongue 21 of the valve flap 20 provides an enlargement of the angle of opening of the valve flap 20, when the tubular body 425 has been advanced by an outer cone 40 and the passage is unblocked for the injected substance or blood collection.

In the seventh embodiment according to FIG. 9, a connection piece 510 is constructed similar to the connection piece 210 of FIGS. 5–5C. On a upper housing part 511, tangentially adjacent lateral wings 524 for fastening on the skin are configured, and a catheter tube 516 is fixedly connected to the front end. A lower housing part 512 is connected to the upper housing part 511 via plug portions 513 and 514, which may be interconnected by ultrasonic welding. In the intermediate space between the two parts, there is a sealing membrane 528 of elastic material the outer edge zone of which has a thickened configuration and which comprises a thick flange edge 530 being inserted into a matching circumferential groove 531 of the lower housing part 512. Integrally formed with the thin-walled center of the sealing membrane 528 is a tubular body 525, whose central bore 527 merges into a hole 532 of the sealing membrane 528. On the front side of the sealing membrane 528, the hole 532 is surrounded by a torus 533 forming the supporting surface 526 for the valve flap 20. The outer ring 22 of the valve flap 20 is clamped between a ring surface 517 of the upper housing part 511 and a surface of the edge zone of the sealing membrane 528.

The rear end of the tubular body 525, which is kept very short, comprises a closed sealing lip 536 having the same task as the sealing lip 236 of the embodiment of FIGS. 5 to 5C and being directed toward the central axis. In its cap-shaped front end, a separate plunger 541 houses the tubular body 525 and centers it on the longitudinal axis of the connection piece 510, so that it is held stably in the sealing membrane in spite of its small diameter and its suspension and does not cant when pushing an elongate member therethrough. Preferably, the plunger 541 is made of firm plastic and guided in the inner cone 515C of the lower housing part 512. An outwardly directed step 535 at the head end of the plunger 541 cooperates with an edge of the lower housing part 512 as a stop preventing the plunger 541 from dropping out. A bore 542 tapering toward the tubular body 525 extends through the plunger 541 from one end to the other. This configuration of the valve device in a connection piece leads to a short structure of the connection piece which, by the cooperation of the valve flap 20, the sealing membrane 528 and the sealing lip 536, has a stable configuration and an excellent sealing function.

What is claimed is:

1. A valve device in a connection piece comprising an open ended flow channel having a valve body arranged therein which is adapted to be brought into an opened position by means of an axially displaceable sliding member, the valve body being configured as a valve flap having a closed surface and being mounted in the connection piece via an elastic radial tongue and resting against an annular supporting surface in a closed position, and the sliding member pivots the valve flap in opening direction about the radial tongue by pressure against the closed surface thereof, the supporting surface being integrally formed with a centrally perforated sealing membrane mounted arranged between the valve flap and the connection piece.

2. The valve device according to claim 1, wherein the sliding member is an outer cone of a coupling assembly or syringe.

3. The valve device according to claim 1, wherein the sliding member is configured as a tubular body being arranged displaceably in the flow channel and being secured against dropping out therein.

4. The valve device according to claim 1, wherein the sealing membrane is a disc of elastomer material.

5. The valve device according to claim 1, wherein the sealing membrane comprises a thick-walled outer flange edge received in an inner circumferential groove of the connection piece.

6. The valve device according to claim 1, wherein the sealing membrane comprises a torus surrounding the central perforation at least on that side facing the valve flap.

7. The valve device according to claim 3, wherein the tubular body is integrally formed with the sealing membrane.

8. The valve device according to claim 3, wherein a radial sealing lip directed inwards within the bore is configured at the rear end of the tubular body.

9. The valve device according to claim 1, wherein the radial tongue connects the valve flap with an outer ring, wherein the tongue, the valve flap, and the outer ring are formed integrally of elastic flat material, and wherein the outer ring is clamped between ring surfaces in the connection piece.

10. Use of the valve device according to claim 1 in combination with a vascular catheter, said valve device having inserted in its flow channel of the connection piece a puncture cannula or mandrin holding the valve flap in opened position without actuating the sliding member.

* * * * *